United States Patent
Knagenhjelm

(10) Patent No.: US 7,409,373 B2
(45) Date of Patent: Aug. 5, 2008

(54) PATTERN ANALYSIS SYSTEM AND METHOD

(75) Inventor: Petter Knagenhjelm, Pixbo (SE)

(73) Assignee: Concepta AB (SE)

( * ) Notice: Subject to any disclaimer, the term of this patent is extended or adjusted under 35 U.S.C. 154(b) by 414 days.

(21) Appl. No.: 10/330,673

(22) Filed: Dec. 30, 2002

(65) Prior Publication Data

US 2003/0153817 A1    Aug. 14, 2003

Related U.S. Application Data

(60) Provisional application No. 60/319,048, filed on Dec. 28, 2001.

(51) Int. Cl.
*G06F 19/00*    (2006.01)

(52) U.S. Cl. .............. 706/20; 706/14; 706/20; 706/21

(58) Field of Classification Search .......... 706/8, 706/10–21, 25, 46–51, 61; 395/10, 20, 21, 395/54, 62, 63, 75, 77
See application file for complete search history.

(56) References Cited

U.S. PATENT DOCUMENTS

| | | | | |
|---|---|---|---|---|
| 5,533,519 A | | 7/1996 | Radke et al. ............ | 128/777 |
| 5,601,090 A | | 2/1997 | Musha ................... | 128/731 |
| 5,691,693 A | * | 11/1997 | Kithil .................... | 340/439 |
| 5,795,306 A | * | 8/1998 | Shimotani et al. ....... | 600/558 |
| 5,810,747 A | | 9/1998 | Brudny et al. .......... | 600/595 |
| 6,006,188 A | * | 12/1999 | Bogdashevsky et al. .. | 704/270 |
| 6,016,449 A | * | 1/2000 | Fischell et al. .......... | 607/45 |
| 6,070,098 A | * | 5/2000 | Moore-Ede et al. ...... | 600/544 |
| 6,090,044 A | | 7/2000 | Bishop et al. ........... | 600/300 |
| 6,248,063 B1 | * | 6/2001 | Barnhill et al. ......... | 600/300 |
| 6,496,724 B1 | * | 12/2002 | Levendowski et al. ... | 600/544 |
| 2002/0091654 A1 | * | 7/2002 | Alroy .................... | 706/21 |

FOREIGN PATENT DOCUMENTS

WO    WO 99/44502 A1    9/1999
WO    WO 00/64347 A1    11/2000

OTHER PUBLICATIONS

Semrud-Clikeman, "Components of Attention in Children with Complex Partial Seizures with and without ADHD", Epilepsia, 40(2): 211-215, 1999.*

(Continued)

*Primary Examiner*—Joseph P. Hirl
*Assistant Examiner*—Omar F Fernandez Rivas
(74) *Attorney, Agent, or Firm*—Ostrolenk, Faber, Gerb & Soffen, LLP

(57) ABSTRACT

Method and arrangement for providing a computerized system having an interface arrangement for interfacing a data source. The data source delivering data related to motion of a person, a memory arrangement for storing said data, a processor for processing the data, an artificial neural network (ANN) using the processor, means for collecting a second set of data from the person, means for calculating one or several parameters distinctive of various features of said person, and means for feeding the parameter values to the ANN trained to recognize the various features.

9 Claims, 3 Drawing Sheets

OTHER PUBLICATIONS

Semrud-Clikeman et al. "Components of Attention in Children with Complex Partial Seizures with and without ADHD", 1999, pp. 211-215.*

Heinrich et al., "Single Sweep Analysis of Event-Related Potentials by Wavelet Networks-Methodological Basis and Clinical Application", 1999, pp. 867-879.*

Heinrich et al. "Single-Sweep Analysis if Event-Related Potentials by Wavelet Networks- Methodological Basis and Clinical Application", 1999, pp. 867-879.*

H. Lee, L. Guan, and J.A. Burne—Human Gait and Posture Analysis for Diagnosing Neurological Disorders. *School of Electrical and Information Engineering, Department of Biomedical Science—University of Sydney,* © 2000, pp. 435-438.

Teewoon Tan, Ling Guan, and John Burne—A Real-Time Image Analysis System for Computer-Assisted Diagnosis of Neurological Disorders. *Real-Time Imaging 5,* pp. 253-269 (1999), Article No. rtim. 1998.0139.

Database Medline 'Online!, US National Library of Medicine (NLM), Bethesda MD., US AN: NLM92649463, "The Use of Kohonen's Neuronal Network For The Analysis of the Psychophysiological Characteristics of Persons with Seasonal Affective Disorders", XP002252904, abstract.

\* cited by examiner

PATTERN ANALYSIS SYSTEM AND METHOD

CROSS REFERENCE TO RELATED APPLICATIONS

The present application claims the benefit of U.S. provisional patent application No. 60/319,048 filed Dec. 28, 2001, the disclosure of which is hereby expressly incorporated by reference in its entirety for purposes of disclosure.

FIELD OF THE INVENTION

The present invention relates to an analysis method and a computerized system for detection and prediction of pattern(s) in data that quantifies details or characteristics of a person (personal data). The resulting pattern(s) can be used to characterize the personal data, and with increased knowledge, refine efficiency in predictions about the person and specific characteristics will be enabled, especially, but not exclusively, with respect to medical therapy.

BACKGROUND OF THE INVENTION

Patients who suffer from some psychological syndromes have different movement patterns than a group of people without psychological syndromes. Patient movements can be measured together with other patient data. If the patient's psychological syndrome can be characterized by measured patient data and the use of an objective analysis method, it would be possible to observe the effect of applied medical therapies. Such analysis method would be very useful.

U.S. Pat. No. 5,810,747 describes an interactive intervention training system used for monitoring a patient suffering from neurological disorders of movement or a subject seeking to improve skill performance and assisting their training. A patient (or trainee) station is used in interactive training. The patient (or trainee) station includes a computer. A supervisor station is used by, for example, a medical or other professional. The patient (or trainee) station and the supervisor station can communicate with each other, for example, over the Internet or over a LAN. The patient (or trainee) station may be located remotely or locally with respect to the supervisor station. Sensors collect physiological information and physical information from the patient or subject while the patient or subject is undergoing training. This information is provided to the supervisor station. It may be summarized and displayed to the patient/subject and/or the supervisor. The patient/subject and the supervisor can communicate with each other, for example, via video, in real time. An expert system and neural network determine a goal to be achieved during training. There may be more than one patient (or trainee) station, thus allowing the supervisor to supervise a number of patients/subjects concurrently.

Another known technique is illustrated in FIG. 1; OPTAx, delivered by OPTAx SYSTEMS, Inc. Continuous Performance Test (CPT) is a fifteen min test to measure inattention and impulsivity. The patient 11 executes the test himself on a computer 12, while the patient's head motions are measured with a camera. The camera finds the head position by tracking a marker 13 that is fitted on the patient's head. Motion data and CPT data are sent to a central system 14 after finalizing the entire test. Test results are calculated on the central system. The results are compiled to a report, which is sent back to a physician. The physician uses the report as one instrument to treat the patient, for example, through the prescription of medication.

A number of new techniques have been described in Proc. of the 7$^{th}$ IEEE Int. Conf. On Image Processing, Sep. 10-13, 2000, Vol. 2, P. 435-438 intended to enhance the performance of a video analysis system, free from motion markers and complicated setup procedures. The system is used for purposes of quantitatively identifying gait abnormalities in static human posture analysis. Visual features are determined from still frame images out of the entire walking sequence. The features are used as a guide to train a neural network in an attempt to assist clinicians in demagnetizing patients with neurological disorders.

The application of digital image processing and pattern recognition techniques are described in Real Time Imaging, Vol. 5, No. 4 (August 1999) p. 253-269 for assisting in diagnosing neurological disorders. In medical practices, the posture and movement of human subject through his/her gait cycle contains information that is used by experienced clinicians to determine the mental health of a patient. This is achieved by processing, extracting and classifying joint angle information from images of a human subject's gait. Joint angles and swing distances obtained from normal and patient subjects are used in training and verifying classifications using feed-forward neural network and a fuzzy clustering algorithm.

In U.S. Pat. No. 6,090,044, a system for diagnosing medical conditions, such as low back pain (LBP), is described whereby a neural network is trained by presentation of large amounts of clinical data and diagnostic outcomes. Following training, the system is able to produce the diagnosis from the clinical data. By comparison, the present invention may be useful in diagnosing LBP in one embodiment, but there are other applications for the present invention both in the medical fields and in other fields. The instant intelligent diagnostic system is less expensive and more accurate than conventional diagnostic methods, and has the unique capability to improve its accuracy over time as more data is analyzed.

According to WO0064347, a pattern is determined of the neck movement of a subject. The head/body movement of the subject is recorded with markers placed on the shoulders and on the head and which therefore move with the subject. The locus curve of each marker in three-dimensional space is then determined in dependence on the time and it is stored as a data set. The neck movement is isolated from the head and torso movements by determining the difference between the average of the two locus curves that represent the shoulder movements and the locus curve representing the head movement. The pattern of movement established on the cranio-corpography is evaluated and analyzed using a data-processing device. The method is particularly suitable for determining the presence and the severity of an injury to the cervical spine as a result of whiplash caused by a traffic accident.

SUMMARY OF THE INVENTION

It is an object of one of the preferred embodiments of the present invention to provide a computer system and an analysis method that distinguishes a personal characteristic, such as a disorder, and preferably, disorders related to some special type of psychological syndrome. Amongst others, the advantages of this embodiment of the invention involve fast, accurate and classified decision and automatic storage of relevant data. The results involve providing more accurate and correct amounts of drugs, allowing the finding/predicting of subgroups of patients that are especially responsive to medication and the like.

For these reasons the present invention includes a computerized system having an interface arrangement for interfacing a data source that delivers data related to motion of a person. A memory arrangement is provided for storing the data and a processor is provided for processing the data. An included artificial neural network (ANN) uses the processor and acts as a means for collecting a second set of data from the person or subject. A means for calculating one or several parameters distinctive of various features of the person is included, as is a means for feeding the parameter values to the ANN trained to recognize the various features or characteristics. Most preferably, the features include psychological syndromes, however, other analysis may also be conducted. In one embodiment, the ANN is trained with data collected from one or several persons being under influence of drugs. Preferably, the ANN includes a number of nodes representing sets of training data. The system may include means for use of Linear Predictive Coding (LPC) to analyze the parameter values fed to the ANN. According to one embodiment, the data source is a camera. Most preferably, the ANN is a Kohonen type ANN.

The invention also relates to a method for the detection of a characteristic of a person employing an artificial neural network (ANN) in which motion data are analyzed and which includes measuring motion data on the person or subject; collecting other measured data from the person; calculating one or several parameters distinctive of various characteristics; feeding the parameter values to an ANN trained to recognize various characteristics, and analyzing the parameter values in the neural network. According to most preferred embodiments, the characteristics include at least one psychological syndrome. The parameters include one or several of the following: the variance of distance, the variance of CPT variables, the residual signal defined as difference between the input signal and a smoothed version of the same, an estimate of immobility duration, and one or more parameters suited to detect periodicity in the one or more of the input signals.

The invention also relates to a method for the detection of patients with psychological syndrome employing an artificial neural network (ANN) in which motion data are analyzed and which include: measuring motion data on a patient; collecting other measured data from the patient; calculating one or several parameters distinctive of various psychological syndromes; feeding the parameter values to an ANN trained to recognize various psychological syndromes, and analyzing the parameter values in the neural network. The parameters exemplarily include one or more of the following: the variance of distance, the variance of CPT variables, the residual signal defined as difference between the input signal and a smoothed version of the same, an estimate of immobility duration, and one or more parameters suited to detect periodicity in the one or more of the input signals. Preferably, the ANN is trained with data collected from patients being under influence of drugs. According to one embodiment, the ANN has a number of nodes representing sets of training data. Most preferably, the ANN is a Kohonen-map type ANN. The method also includes the use of linear predictive coding (LPC) to analyze the parameter values fed to the ANN. The parameters are used for optimal correlation between parameter distance and conceptual distance. Preferably, the psychological syndrome is ADHD.

Further objects of the invention will be evident from the following description of the invention, the attached drawings illustrating an exemplary and preferred embodiment, the detailed description thereof, and the appended claims.

DESCRIPTION OF THE DRAWINGS

The invention will be described in the following with reference to attached exemplary drawings, in which.

DETAILED DESCRIPTION

To simplify the description of the present invention, the following definitions are used which are based on a system for patient analyses; however, the invention is not limited to such a system:

Model

To distinguish between different signal patterns, a model is used to characterize typical qualities and features of the patient data. The model parameters are chosen with the aim to be as distinct, unambiguous and informative as possible. The set of parameters shall reflect the typical signal patterns.

In addition, to be sensitive to psychological syndrome characteristics, it is important that the parameters shall be insensitive to features irrelevant to the task.

EventDistanceLimit:

Minimum distance (eucledian) traveled before it is considered to be a movement.

For example: EventDistanceLimit=1 mm

Microevent:

From any point on the movement trajectory, a Microevent is said to occur when the first following point along the trajectoria is reached, where the Eucledian distance between the two points exceeds EventDistanceLim.

Feature Vector

Figure 4:
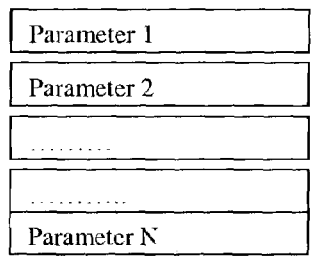
FIG. 4 is an exemplary depiction of a vector illustration.

The values of the model parameters (see FIG. 4) are compiled to form a vector, below named the feature vector. For each subset of patient data, the values of the feature vector are extracted.

Prior to the extraction of parameter values, the signal mean is separate for some signals. The mean will vary with patients and/or hardware and may not contain useful information. The mean is therefore removed in those cases. Each k-dimensional feature vector can be regarded as one point in a k-dimensional signal-space.

Training

An Artificial Neural Network (ANN) is iteratively trained to organize groups or clusters of feature vectors with similar properties. The self-organizing process, known as Self-Organizing Feature Map (SOFM), for example as described in T. Kohonen's *Phonetic typewriter for Finnish and Japanese*, has shown great capability of performing this task.

The number of clusters is defined prior to the training and is determined by the required resolution of the ANN. The training is initiated by a set of (for example M) clusters, randomly positioned in the k-dimensional signal-space.

Compiling the feature vectors from a large number of patients forms the database used for training. During the training, each input feature vector is compared to each cluster to find the one with best resemblance to the input vector. This cluster is voted winner, and is adjusted towards the input vector. In addition, all other clusters within a neighborhood to the winner in another domain, the so-called map-space, are adjusted towards the input vector. The map-space is usually of low dimension containing a node for each cluster in the signal-space. The nodes are arranged in hexagonal or a square lattice, and the Euclidean distance between them defines their internal relation. A node's neighborhood is usually defined by a neighborhood function and contains the set all nodes in the beginning of the training whereas only a few (or none) are considered neighbors at the end. The further away a node is from the winner in the map-space, the less the corresponding cluster in the signal-space is adjusted towards the input vector. Thus, all adjustments are done in the signal-space, while the rules of adjustments are defined in the map-space.

The training time is predetermined and an annealing function is used to "freeze" down the system causing only small adjustments at the end of the training. The neighborhood function creates correlation between the signal-space distance and the map-space distance allowing classification to be performed in the (low dimensional) map-space, rather than in the more complicated signal-space.

The method described above is known as "unsupervised learning", that is, there is no need to use classified data in the training procedure described above.

When the ANN is readily trained, the clusters will represent features of the input signal including normal and various types of psychological syndrome characteristics.

Figure 5:
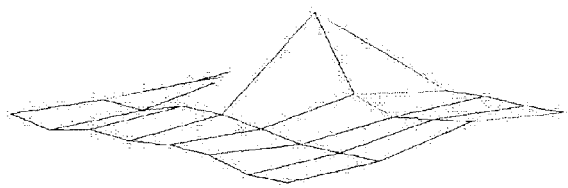
FIG. 5 is an exemplary depiction of a map response illustration.
Figure 5:
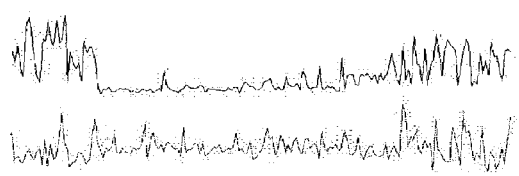

The response (output) of the ANN is proportional to the signal distance between the input signal and all the clusters (see FIG. 5). Often, this output is of less interest in the case of classification. The output is instead used to find the node with best resemblance to a classified input. This is known as the labeling phase in the design of the ANN. Features with known qualities are presented for the ANN, the output is observed and the node giving the highest output is labeled with the presented feature. The actual output thereafter is the label rather than the response value.

The set of clusters are now stored and can then be used in the analysis in runtime mode. Patient data is analyzed exactly the same way as done in the training phase to extract the values of the parameters used in the model, for example, the feature vector. The vector is then presented to the network, which will produce the output label (classification).

In summary, the present invention, in its primary embodiments, is based on the understanding that an analysis of patient data with an Artificial Neural Network (ANN) can successfully be used to distinguish between patients with psychological syndromes and normal patients.

Thus, the present invention provides an Analysis Method (AM) in which patient data, consisting of motion data and other data measured from the patient, is used for calculation of a number of parameters. Patient data are collected from a large number of patients and the data is used to train ANN to teach the system the variation ranges of the parameters. The result from the ANN is obtained as a low-dimensional chart in which each set of patient data is represented by a trajectory. A trajectory for a normal patient looks very different from that for a patient with psychological syndromes.

In particular, an exemplary method performed according to the present invention includes a selection from the following steps:

Measuring motion data such as position of the patient or a part of the patient's body as a function of time;
Collecting other measured data from the patient;
Calculating one or several parameters distinctive of patients with psychological syndrome;
Feeding the parameter values to the artificial neural network trained to recognize psychological syndrome characteristics; and Analyzing the parameter values in the neural network.

Figure 1:
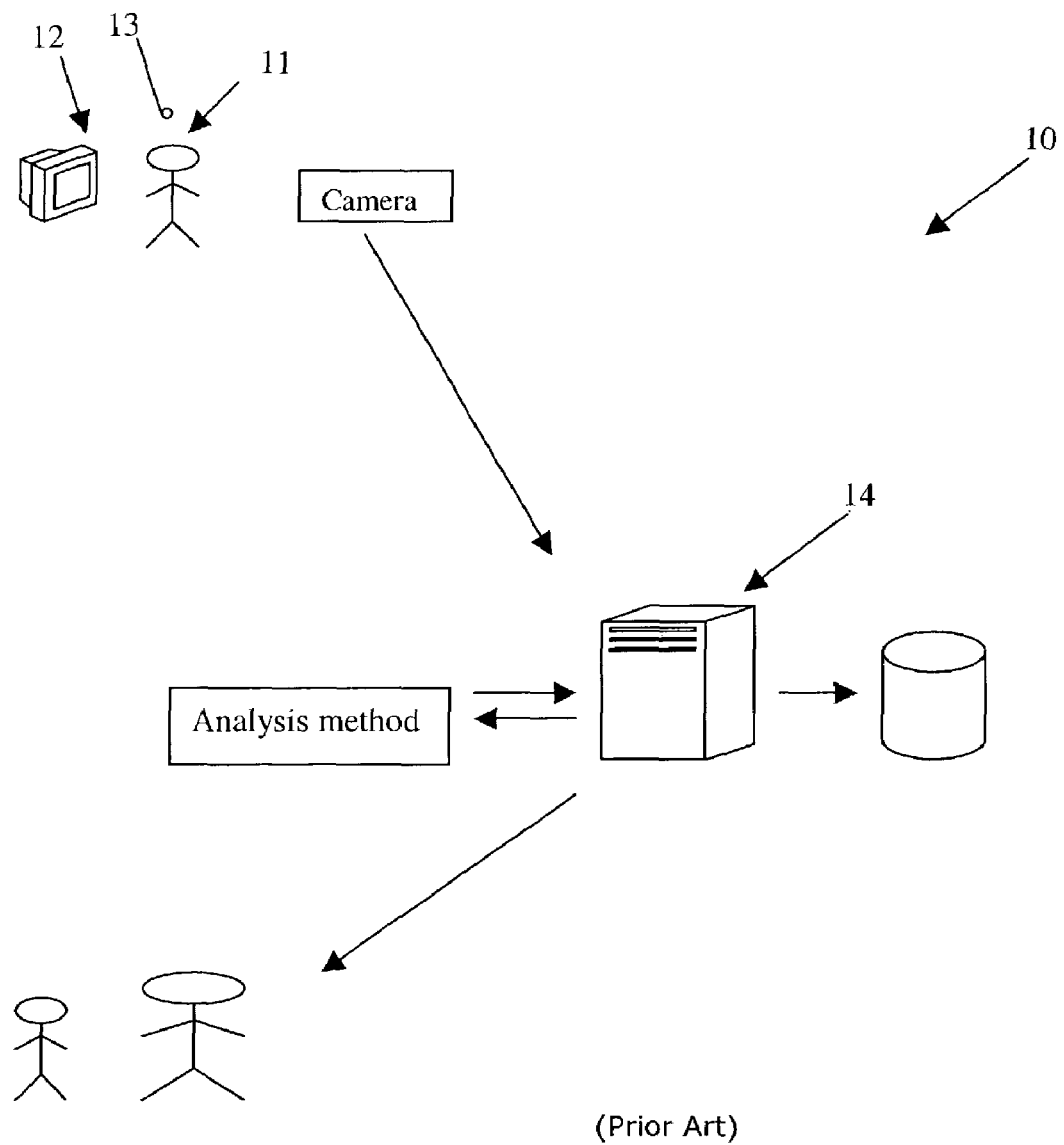
FIG. 1 is a schematic representation of a known system.
Figure 2:
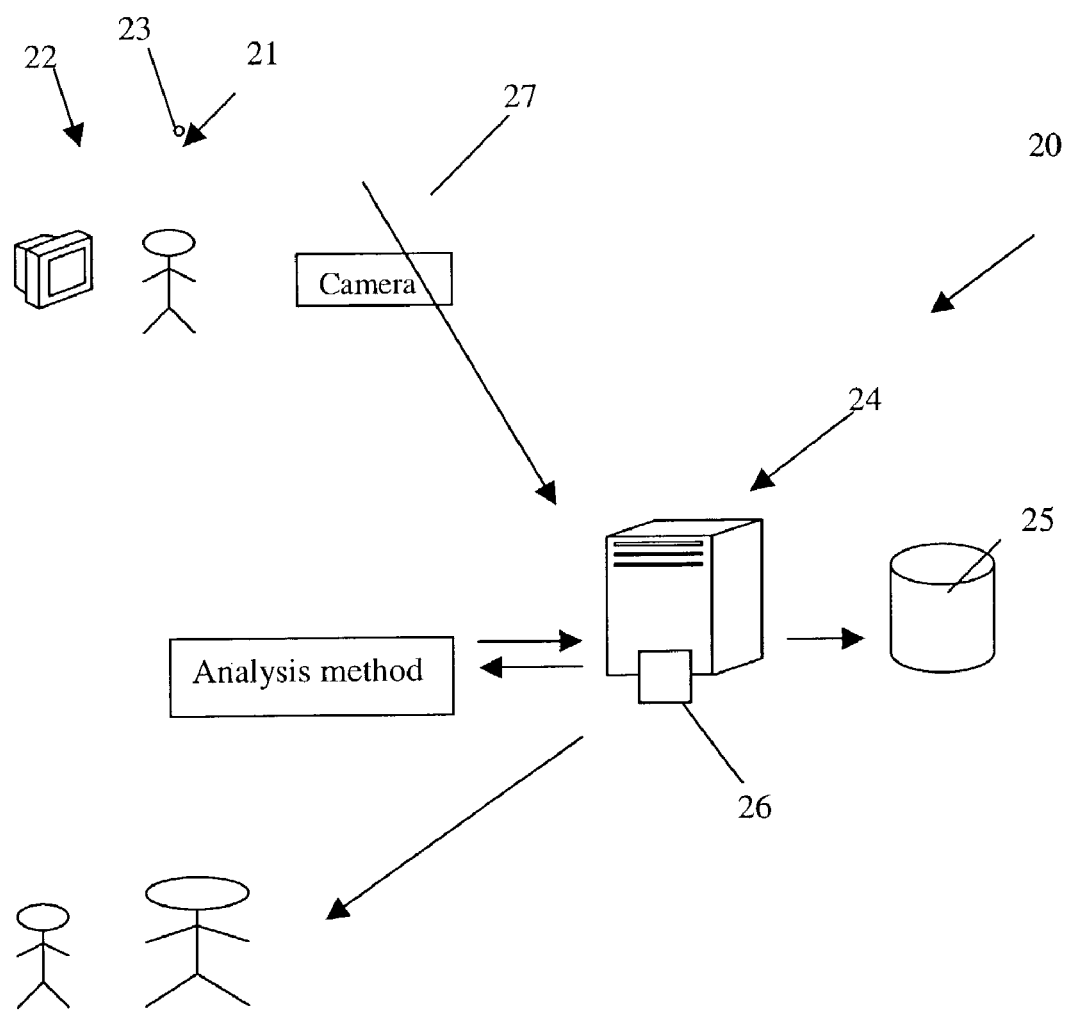
FIG. 2 is a schematic representation of a system configured according to the present invention.

An exemplary and preferred embodiment of a system 20 configured according to the present invention is illustrated in FIG. 2 in which a computer unit or other training arrangement 22, a central unit 24 connected to a database 25 and comprising AM 26 with an ANN, a camera unit 27 and an interface means (not shown) for communication between various parts are incorporated. The person, patient, or other subject is provided with a marker 23. The central unit is a conventional computer comprising memory, interface, drivers, storage means, and the like. For the purpose of the invention, especially for ADHD, the marker is placed on the head of the person to be analyzed and the motion of the head is analyzed.

The Artificial Neural Network (ANN) 26 is preferably trained with data collected from a large number of patients 21. The data is collected from patients differing in many aspects: sex, age, medical drugs, movement pattern, type of psychological syndrome, and the like. The parameter values can be analyzed using a Linear Predictive Coding.

The collected data form a primary database 25. During the training of the artificial neural network, the data is quantified under formation of a small secondary dedicated database, which is used in AM. Thus, according to the present invention, a dedicated secondary database obtained from a primary database comprising data collected from a large number of persons is used in AM. Most specially, the invention offers a new approach as the patients are analyzed and data is collected under the influence of drugs, which is compared to a first collected (system training) data. The patients are analyzed using a reaction test and by analyzing movement patterns, especially movement of the patient's head that is preferably tracked using a detectable arrangement such as a marker. The approach of testing a patient under influence of drugs is thus unique for the invention.

Moreover, the performance of the patient can be measured while analyzing the movement pattern. That is, the performance of the patient can be measured utilizing a switch that can be set between on and off positions, thereby giving a reaction time. The performance test can be conducted by providing a patient with very tedious and monotonous tasks or tests so that the characteristic capacities of a patient are exposed. For example, two different images can be shown in random order, whereby the person to be analyzed must activate the switch for one image and not activate the switch for the other image. The reaction time, number of correct and wrong decisions, and movement pattern can be measured during the test. The result of the test can be used as a basis for a screening report.

The system can also generate a treatment report that is specially arranged to objectively group different types of psychological syndromes, most preferably for ADHD related syndromes. The groups are completely based on the objective measurement data. Some groups react positively to a drug and some in a negative way, thus the test under drug influence. Through grouping the patients, it is possible to diagnose correct treatment. It is also possible to measure the accuracy of a drug dose.

In the system, the ANN includes a number of nodes representing sets of training data. Each node reflects a state or an incident (feature). Neighboring nodes represent incidents of similar features. In the same way as in training, a feature vector is extracted for each subset of data. The Euclidean distance from the feature vector to each node is calculated. The node in closest proximity to the vector is associated with it. Sequences of incident vectors are followed as sequences of nodes in the artificial neural network. It can be said that a sequence of nodes is the response from the network. Thus, a trajectory in the structure of the network (response) is followed rather than in the parameter space. The fact that the dimension of the network more often is smaller than the parameter space is of advantage, since the calculation thereby is simplified. The response from the network forms the basis for distinguishing between patients with psychological syndrome and normal patients.

The ANN 26 is based on a self-organizing process, known as Self-Organizing Feature Map (SOFM). This type of ANN is preferable to use in this application compared to the other types of ANN, for example MLP neural networks, due to the fact that there is no need for supervised training. The use of unsupervised training makes the training easier to handle large amount of data, less labor intensive and objective. After the training is finalized, the output of the ANN can be labeled with a small amount of classified data. An additional advantage with SOFM ANN is that neighboring nodes in the ANN output represents similar features of the input signal. This implies that the output can be interpreted as a continuum (c.f. soft decision) rather than on-off (c.f. hard decision).

The result from the ANN is presented to competent persons (e.g. physician) by mail, e-mail, through Internet, displayed on a display and the like.

Further variations of the present invention are disclosed in the following description of a preferred embodiment.

EXAMPLE 1

Application on Patient Data

Equipment: Measuring system from OPTAx, a PC with software based on this analysis method.

Patients: X patients aged from YEARS a to YEARS b, suffering from the psychological syndrome, ADHD, and Y normal patients.

Measurement: The patient was set up with a device for measuring the patient motion during a continuous performance task (CPT). Motion coordinates and data from the CPT were collected. The measuring time was 15 minutes. Motion data was sampled at 50 Hz, and performance data at 0.5 Hz.

EXAMPLE 2

Implementation

Data Acquisition

Figure 3:
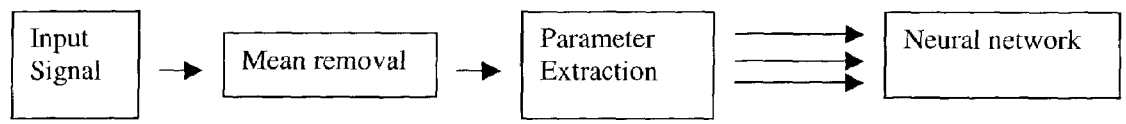
FIG. 3 is a block diagram illustrating certain functional features of the present invention.

Referring to FIG. 3, assume that the input signal(s) is a digitized version of the measured signal(s). Each signal is sampled at a certain rate, giving a sequence of samples according to:

$x_i, i=0,1,\ldots,N$

Pre-Processing

To reduce the influence of individual patient variations and to facilitate classification stability, some signals should pass a device to remove the signal mean. Any kind of steep edge high-pass filter can be employed.

Parameters

A window is used to calculate parameters on a subset of the data at a time. The window is then slid over the entire measurement. The parameters extracted may be one or more of (but not limited to) the following.

The variance of distance, d, which is defined as $$\frac{1}{N-1}\sum_{i=1}^{N}(d_i-\bar{d})^2,$$

where the distance, d, is defined as the Euclidean distance between two consecutive sample points of motion data, N the number of samples of the complete measurement, and $\bar{d}=1/N\cdot\Sigma_{i=1}^{N}d_i$, i.e. the mean movement per sample in meters.

The variance of CPT variables such as latency defined as $$\frac{1}{N-1}\sum_{i=1}^{N}(t_i-\bar{t})^2,$$

where the latency, t, is the delay or reaction time, and $\bar{t}=1/N\cdot\Sigma_{i=1}^{N}t_i$, i.e. the mean latency per sample in milliseconds.

The residual signal defined as difference between the input signal and a smoothed version of the same.

An estimate of immobility duration.

One or more parameters suited to detect periodicity in the one or more of the input signals.

Feature Map Geometry and Definitions

Let the M k-dimensional map nodes be denoted $m_i, i=0,\ldots,M-1.$

Most often, the nodes are arranged in a square (2-dimensional) grid. The distance between two map nodes i and j, is denoted $D_{i,j}$ and defined as the squared Euclidean distance ($L^2$ norm) between them in the map-space.

$D_{i,j}=L^2(m_i,m_j).$

This measure is used in the neighborhood function.

Let the input feature vector, representing sample $x_n$ be denoted $y_n$. Furthermore, let the map response in node i for feature n, $S_{i,n}$, be defined as:

$S_{i,n}=e^{-(d_{i,n}^2/k)}$ where the signal-space distance $d_{i,n}^2$, is defined as $$d_{i,n}^2=\sum_{l=1}^{k}w_l(y_l^n-m_l^i)^2$$

and $w_i$ is some suitable weight function.

Annealing Function

The task of the annealing function is to obtain equilibrium at the end of the training. The principle is that large adjustments are allowed in the beginning of the training whereas only small (or zero) adjustments are allowed at the end. How the decrease is incorporated is not critical. Linear, exponential, and even pulsating decay schedules are proposed in the literature.

Initialization

Traditionally, all data driven clustering schemes, including ANNs, employ random positioning of clusters in the signal-space, by assigning (small) random numbers to the parameters. The actual values are not important as long as they are not identical. The ordering of the clusters is also at random.

Training

The iterative algorithm adjusts all clusters after each input feature vector, $y_n$, presented. The direction of the adjustment is towards $y_n$, and how much is determined partly by the annealing function, partly by the neighborhood function. The adjustment formulae for cluster $m_i$ at time instant t+1 is:

$$m_i(t+1)=m_i(t)+\gamma_i(t)\cdot(y_n-m_i(t)), i=0,\ldots M-1$$

where $$\gamma_k(t)=f(t)\cdot g(t)$$

and $f(t)$ is the annealing function and $g(t)$ is the neighborhood function. Various suitable functions are discussed in P. Knagenhjelm's *A recursive design method for Robust Vector Quantization*.

Other parameters used can be, but need not to be limited to:

Microevents
: The number of position changes greater than EventDistanceLim.

Immobility duration
: The average time between Microevents.

Temporal scaling
: Measures the distribution of Immobility duration.

Event Distance
: Euclidian distance sampled at Microevents.

Euclidian Distance
: Euclidian distance sampled at system sampling rate.

Area
: Total area (in mm2) covered during the test period.

AreaTrend
: A measure of how the covered area varies over test time. The area is measured in three or more sub-intervals. The values are used to fit a curve describing the area evolution. The curve fit may be, for example, polynomial or exponential.

Fractal
: A measure of trajectoria complexity.

Latency
: Reaction time, i.e. time between target presentation and response.

Commission Latency
: As above, but measured at commission errors, i.e. at button presses without target present.

LatencyVariation
: Standard deviation of Latency.

Coefficient of Variation
: C.O.V=100*LatencyVariation/Latency

Commission Errors
: Measures rate of incorrect (switch) button presses.

Omission Errors
: Measures rate of incorrect non-presses.

MultiResponse
: Measures multiple responses to a single target.

The invention is not limited to the illustrated and described embodiments. It should be appreciated that variations and modifications may occur and still be within the scope of the attached claims.

The invention claimed is:

1. A method for the detection of a characteristic of a person by means of a computer which generates a report placing said person in a special category in need of treatment, said computer employing a trained artificial neural network (ANN) in which motion data are analyzed, said method comprising:
   measuring motion data from said person;
   collecting other measured data from said person, under influence of a drug;
   calculating the values of one or several parameters distinctive of various characteristics;
   feeding said parameter values to said ANN trained to recognize said various characteristics;
   analyzing said parameter values in said trained ANN;
   wherein said parameters comprise at least the variance of continuous performance task (CPT) variables, said variance of CPT variables comprising variance of latency t defined as:

$$\frac{1}{N-1}\sum_{i=1}^{N}(t_i-\bar{t})^2$$

where the latency t is the delay or reaction time, N being the number of samples of the complete measurement, and $$\bar{t}=\frac{1}{N}\cdot\sum_{i=1}^{N}t_i.$$

2. The method of claim 1, wherein said characteristics include at least one psychological syndrome.

3. In a computerized system, a method for the detection of patients with ADHD employing a trained artificial neural network (ANN) in which motion data are analyzed, said method comprising:
   measuring motion data on a patient;
   collecting other measured data from the patient;
   calculating, from said motion data and other measured data, the values of one or several parameters distinctive of ADHD;
   feeding said parameter values to said ANN trained to recognize ADHD;
   analyzing said parameter values in said trained ANN; and
   wherein said parameters comprise: the variance of distance, the variance of continuous performance task (CPT) variables, the residual signal defined as difference between the input signal and a smoothed version of the same, an estimate of immobility duration, and one or more parameters suited to detect periodicity in the one or more of the input signals; said variance of CPT variables comprising variance of latency t defined as:

$$\frac{1}{N-1}\sum_{i=1}^{N}(t_i-\bar{t})^2$$

where the latency t is the delay or reaction time, N being the number of samples of the complete measurement, and $$\bar{t}=\frac{1}{N}\cdot\sum_{i=1}^{N}t_i.$$

4. The method of claim 3, wherein said ANN is trained with data collected from patients being under influence of drugs.

5. The method of claim 3, wherein said ANN comprises a number of nodes representing sets of training data.

6. The method of claim 3, wherein the ANN is a Kohonen-map type ANN.

7. The method of claim 3, further comprising the use of linear predictive coding (LPC) to analyze the parameter values fed to the ANN.

8. The method of claim 3, wherein said parameters are used for optimal correlation between parameter distance and conceptual distance.

9. A method for the detection of a characteristic of a person by means of a computer which generates a report placing said person in a special category in need of treatment, said computer employing a single trained artificial neural network (ANN) in which motion data are analyzed, said method comprising:
  measuring motion data from said person;
  collecting other measured data from said person, under influence of a drug;
  calculating the values of one or several parameters distinctive of various characteristics;
  feeding said parameter values to said ANN trained to recognize said various characteristics;
  analyzing said parameter values in said trained ANN;
wherein said parameters comprise: the variance of distance, the variance of continuous performance task (CPT) variables, the residual signal defined as difference between the input signal and a smoothed version of the same, an estimate of immobility duration, and at least one additional parameter suited to detect periodicity in the one or more of the input signals; said variance of CPT variables comprising variance of latency t defined as:

$$\frac{1}{N-1}\sum_{i=1}^{N}(t_i - \bar{t})^2$$

where the latency t is the delay or reaction time, N being the number of samples of the complete measurement, and $$\bar{t} = \frac{1}{N} \cdot \sum_{i=1}^{N} t_i.$$

* * * * *